United States Patent [19]

Kosky et al.

[11] Patent Number: 4,649,210

[45] Date of Patent: Mar. 10, 1987

[54] REDUCING PHOSGENATION REACTION TEMPERATURES

[75] Inventors: Philip G. Kosky, Schenectady; James M. Silva, Clifton Park; Daniel J. Brunelle, Scotia; Thomas G. Shannon, Schenectady, all of N.Y.

[73] Assignee: General Electric Company, Schenectady, N.Y.

[21] Appl. No.: 778,820

[22] Filed: Sep. 23, 1985

[51] Int. Cl.[4] ............... C07C 68/02; C07C 69/96
[52] U.S. Cl. ................... 558/265; 558/268; 558/281; 558/282
[58] Field of Search ............... 558/268, 277, 265, 281, 558/282

[56] References Cited

U.S. PATENT DOCUMENTS

| | | | |
|---|---|---|---|
| 4,025,489 | 5/1977 | Bailey et al. | 558/268 X |
| 4,089,888 | 5/1978 | Tokumitsu et al. | 558/268 |
| 4,255,557 | 3/1981 | Megumi et al. | 528/196 |

*Primary Examiner*—Bernard Helfin
*Attorney, Agent, or Firm*—Francis T. Coppa; James C. Davis, Jr.; James Magee, Jr.

[57] ABSTRACT

A method is provided for reducing the reflux temperatures of methylene chloride in phosgenation reactions by introducing a second inert vaporizable component to the reaction medium. This second inert vaporizable component has a lower vaporization temperature than the methylene chloride so as to reduce the temperature of vaporization of the mixture. More efficient use of phosgene is obtained when polymerizing aromatic dihydroxy compounds to polycarbonates and higher yields of monomeric and dimeric bischloroformates are obtained.

11 Claims, No Drawings

REDUCING PHOSGENATION REACTION TEMPERATURES

This invention relates to a method for reducing the temperature at which phosgenation reactions take place. More particularly, it relates to methods for preparing chloroformates and polycarbonates by phosgenation reactions at reduced temperatures.

Both polycarbonates and chloroformates are known classes of organic compounds. Polycarbonates are known for their good engineering properties and inherent flame resistance. These polycarbonates can be obtained by reaction of aromatic dihydroxy compounds, such as bisphenol-A, with phosgene. The chloroformates, in particular, bischloroformates of dihydroxy compounds and their oligomers, are known to be useful for the production of polycarbonates. They may also be used as intermediates in the preparation of cyclic carbonate oligomers which may in turn be converted to very high molecular weight polycarbonates. A more detailed description of this chemistry appears in pending, commonly assigned, application Ser. No. 609,407 filed May 11, 1984, now abandoned, the disclosure of which is incorporated herein by reference.

There are a number of known methods for preparing chloroformates and polycarbonates by reaction with phosgene. Each reaction is normally conducted interfacially; that is, in a mixed aqueous-organic system which results in the recovery of the polycarbonate in the organic phase. For detailed descriptions of phosgenation reactions which provide polycarbonates, reference is made to the following U.S. Pat. Nos. 3,155,683, 3,274,214, 3,386,954, 3,422,119, 4,129,574, 4,216,305, 4,197,394, 4,360,659, 4,224,434 and to the procedures described in Encyclopedia of Polymer Science and Technology, *Polycarbonates* (1969) Vol 10, pp. 710–764, Interscience Publishing.

A number of methods of making chloroformates by phosgenation reactions are known in the art. For example, U.S. Pat. Nos. 3,312,661, 3,959,335, 3,974,126 and 3,966,785 prepare bischloroformate compositions by reacting a water soluble salt of an alkylidene diphenol with phosgene in an aqueous system employing an organic diluent. Organic solvents are used in other processes, such as that disclosed in U.S. Pat. No. 3,255,230, where a dihydric phenol is reacted with phosgene in the presence of a quaternary ammonium catalyst. In copending, commonly assigned application Ser. No. 676,353, filed Nov. 29, 1984, and now abandoned a low temperature, low pH synthesis of bischloroformates is described. This application is incorporated herein by reference.

Despite the numerous alternatives for preparing chloroformates and polycarbonates, commercial processes generally utilize an interfacial polycondensation process with methylene chloride as the organic solvent phase. Methylene chloride is generally desirable for its non-flammability, low toxicity, suitable volatility, and moderate cost.

Phosgenation reactions are highly exothermic and require the removal of significant quantities of heat from the reaction solution to ensure high yields of product. Passing a reaction solution which contains polymer product through a conventional heat exchanger often results in clogging due to precipitation of solids on heat exchange surfaces. Therefore, commercial phosgenation processes generally operate at the refluxing temperature for the methylene chloride solvent system so as to generate a condensate which is substantially free of polymer. This condensate is returned to the system so as to maintain a constant temperature during a production run.

Although adequate yields of both polycarbonates and chloroformates are obtained from present processes, operating at temperatures below the refluxing temperature of methylene chloride (about 41° C.) will provide beneficial results. For example, in copending application Ser. No. 676,353 it has been shown that higher yields of monomeric and dimeric bischloroformates are obtained from bischloroformate syntheses where phosgenation temperatures in the range of about 10°–40° C. are used. In addition, Seidell has shown that the solubility of phosgene in chlorinated organic solvents increases as the temperature of the system is lowered in *Solubilities of Organic Compounds,* Vol. II (1941). Increasing the solubility of phosgene in methylene chloride during polycarbonate synthesis will improve phosgene usage since large concentrations of the phosgene are available to react with bisphenol-A. Therefore, it is desirable to operate at reduced temperatures in these phosgenation reactions. It is most desirable to reduce the operating temperature but still continue to generate a condensate. This can be accomplished where the reflux temperature of methylene chloride is reduced below 41° C. Preferred phosgenation temperatures fall within the range of about 10°–30° C. with 10°–20° C. being most preferred for bischloroformate and 20°–30° C. being most preferred for polycarbonate.

Conventional methods for altering the reflux temperature of a liquid is to vary the pressure within the system. However, due to the toxic nature of phosgene, operation at supra-atmospheric conditions is hazardous and operation at sub-atmospheric pressure is precluded because vented scrubbers are required to removes excess phosgene. When operating at atmospheric pressure, the solvent saturation temperature (reflux temperature) controls the reaction temperature. Replacing the methylene chloride solvent with one having the desired volatility is typically not a viable solution in that other properties of the solvent take precedence, such as inertness, flammability, solubility of components, toxicity, etc.

A method is desired which would permit reduction of the phosgenation temperature at atmospheric pressure without significantly changing the methylene chloride solvent utilized. An object of the present invention is to provide a method for decreasing the reflux temperature for methylene chloride during phosgenation reactions when operating at atmospheric pressure. Another object of the present invention is to provide a method which enhances the yield of chloroformate produced without significantly affecting the reaction system. Still a further object of the present invention is to provide a method for reducing phosgenation temperatures which can be conveniently integrated into existing processes. Other objects will be obvious from a detailed description which follows.

The primary aspect of the present invention is a method for reducing the reflux temperature for phosgenation reactions in methylene chloride by adding an inert vaporizable component, such as a refrigerant, to the solvent system utilized. These inert vaporizable components must have a boiling point at atmospheric pressure below that of methylene chloride. The boiling point of methylene chloride is reduced as approximated by Raoult's Law for miscible components, wherein the following equation defines total pressure for ideal conditions:

Total Pressure $= x_1 \cdot VP_1 + x_2 \cdot VP_2 +$ etc.

where $x_1$ and $x_2$ are the mole fractions and $VP_1$ and $VP_2$ are the vapor pressures of miscible components 1 and 2, respectively.

Inert vaporizable components suitable for use in this invention do not participate in the phosgenation reactions, do not react with any of the components present, are non-toxic and non-flammable so as not to detract from the benefits of a methylene chloride solvent system. Examples of suitable inert vaporizable components are inert fluorocarbon refrigerants having a boiling point in the range of about $-10°$ C. to $30°$ C. These include halogenated fluorocarbons such as $CCl_3F$, $CHCl_2F$, $CClF_2—CClF_2$, $CCl_2F—CF_3$, $CH_2Cl—CF_3$, $CH_3—CClF_2$, $CBrClF_2$, $CF_2I—CF_3$, $CHClF—CClF_2$, and the like, perfluorinated carbon compounds of from 4 to 5 carbon atoms and fluorinated ethers of from 2 to 4 carbon atoms; examples of which include n-perfluorobutane, perfluoroisobutane, cyclic-octafluorobutane, tetrafluorodimethyl ether, perfluorodiethyl ether, 1,1-difluorodimethyl ethers, etc. Mixtures of such refrigerants are also suitable. Those fluorocarbon refrigerants which have a boiling point below $15°$ C., such as $CClF_2—CClF_2$, are preferred. Other inert vaporizable components and refrigerants which satisfy the boiling point and vapor pressure requirements described above are suitable and are considered within the scope of this invention. Such vaporizable components and refrigerants will be obvious to those skilled in the art. Fluorocarbon refrigerants with a boiling point below $-10°$ C. are difficult to recover and large quantities are required for those with boiling points above $30°$ C.

The quantity of fluorocarbon refrigerant utilized typically falls within the range of about 1 to 50 wt. % of the total solvent. Quantities of fluorocarbon refrigerant below 50 wt. % are desirable in that the reactants and products are typically insoluble in these compounds. Quantities less than 1 wt. % are generally ineffective. The fluorocarbon refrigerants are preferably soluble in the organic solvent utilized in that the formation of a separate phase may interfere with the interfacial reaction. The fluorocarbon refrigerants recited above are generally soluble within methylene chloride.

Other than reducing the temperature of reaction, the phosgenation reactions proceed in the usual way. The fluorocarbon refrigerants can be introduced with solvent in a conventional reaction scheme and the vaporized fluorocarbon refrigerants can be recovered and returned as liquids to the reaction with the methylene chloride solvent.

Although volatile compounds other than the halogenated fluorocarbons, perfluorinated carbon compounds and fluorinated ethers described herein can affect the vaporization temperature of methylene chloride, these alternative compounds either have higher volatilization temperatures, are flammable, toxic or antisolvents. For example, most of the alternative solvents for polycarbonate synthesis have volatilization temperatures above that of methylene chloride and are often flammable or toxic.

Phosgene is ordinarily introduced to a mixture of reactant and solvent as a gas, but its introduction as a liquid or in solution is within the scope of this invention. The quantity of phosgene utilized typically ranges from about 1.0 to 2.5 equivalents per equivalent of reactant. Lower values within this range are preferred. The phosgene flow rate can vary widely and is not critical to the performance of this invention, but a value within the range of about 0.01 to 0.2 equivalents per equivalent of reactant per minute is usually preferred when preparing chloroformates at temperatures below about $25°$ C. The reflux temperature for the solvent is preferably in the range of $10°-20°$ C. when producing chloroformates.

In producing chloroformates by the method of this invention, the reactant is typically a hydroxy compound of the formula $R^2(OH)_x$ wherein $R^2$ is an aliphatic, alicyclic or aromatic radical and x is a least 1, said solution being maintained at a reflux temperature within the range of about $15°-20°$ C. with the use of the fluorinated compounds. The illustrative examples of dihydroxy compounds include ethylene glycol, propylene glycol, trimethylene glycol, tetramethylene glycol, hexamethylene glycol, dodecamethylene glycol, poly-1,4-(2-butenylene)glycol, poly-1,10(2-ethyl decalene)glycol, 1,3-cyclopentanediol, 1,3-cylcohexanediol, 1,4-cylcohexanediol, resorcinol, hydroquinoline, 4,4'-dihydroxy-diphenyl, bisphenol-A and 1,4-bis(hydroxymethyl)benzene. Also included are the hydroxy aromatic compounds listed below:

4,4'-dihydroxy-diphenyl-1,1-butane;
4,4'-dihydroxy-diphenyl-1,1-isobutane;
4,4'-dihydroxy-diphenyl-1,1-cyclopentane;
4,4'-dihydroxy-diphenyl-1,1-cyclohexane;
4,4'-dihydroxy-diphenyl-phenyl methane;
4,4'-dihydroxy-diphenyl-2-chlorophenyl methane;
4,4'-dihydroxy-diphenyl-2,4-dichlorophenyl methane;
4,4'-dihydroxy-diphenyl-p-isopropylphenyl methane;
4,4'-dihydroxy-diphenylnaphthyl methane;
4,4'-dihydroxy-diphenyl-2,2-propane;
4,4'-dihydroxy-3-methyl-diphenyl-2,2-propane;
4,4'-dihydroxy-3-cyclohexyl-diphenyl-2,2-propane;
4,4'-dihydroxy-3-methoxy-diphenyl-2,2-propane;
4,4'-dihydroxy-3-isopropyl-diphenyl-2,2-propane;
4,4'-dihydroxy-3,3'-dimethyl-diphenyl-2,2-propane;
4,4'-dihydroxy-3,3'-dichloro-diphenyl-2,2-propane;
4,4'-dihydroxy-diphenyl ether.

The preferred diols are those in which $R^2$ is aromatic and especially bisphenols having the formula: HO—$A^1$—Y—$A^2$—OH, wherein $A^1$ and $A^2$ are a single-ring divalent aromatic radical and Y is a bridging radical in which one or two atoms separate $A^1$ from $A^2$. The $A^1$ and $A^2$ values may be unsubstituted phenylene or substituted derivatives thereof, such as, alkyl, alkenyl, vinyl, allyl, halo, nitro, alkoxy, phenyl, and the like. Both $A^1$ and $A^2$ are preferably p-phenylene although both may be o- or m-phenylene. The bridging radical, Y, is one in which one or two atoms, preferably one, separate $A^1$ from $A^2$. It is most often a hydrocarbon radical and particularly a saturated radical such as methylene, cyclohexylmethylene, cyclododecylmethylene, ethylene, 2,2-propylene, 1,1-cyclohexylene, and the like. Also included, however, are unsaturated radicals and radicals which are entirely or partially composed of atoms other than carbon and hydrogen, such as 2,2-dichloroethylidene. The preferred reactant is 2,2-bis(4-phenylene)(propylidene) radical, which is derived from bisphenol-A, wherein each of $A^1$ and $A^2$ is p-phenylene and Y is 2,2-propylidene. By preparing chloroformates at lower temperatures by this process, higher yields of low molecular weight chloroformates are obtained which, in turn, provide low molecular weight cyclic carbonates of a low melt viscosity.

In preparing polycarbonate polymers, the reactant is typically a bisphenol as described above having the formula HO—$A^1$—Y—$A^2$—OH, wherein Y, $A^1$ and $A^2$ are as defined above. Reaction takes place in the presence of an interfacial polycondensation catalyst to generate the polymer. The most preferred reactant is bisphenol-A. The phosgene flow rate is typically in the range of 0.01 to 0.2 equivalents per equivalent of reactant per minute. The reflux temperature is preferably in the range of 10°–30° C. and most preferably 20°–30° C. when producing polycarbonates. Pressures of about 1 atmosphere are preferred. These low temperature conditions enhance phosgene usage by increasing the solubility of phosgene in methylene chloride permitting more to react with bisphenol-A.

The following examples illustrate particular embodiments of this invention. These examples are not provided to restrict the scope of this invention to their contents.

EXAMPLE 1

A 2-liter Morton flask, charged with bisphenol-A (114.14 g; 0.50 mol), methylene chloride (400 ml) and fluorocarbon refrigerant 114 ($C_2Cl_2F_4$; 100 ml), was fitted with a chilled spiral condenser (condenser temperature = $-6°$ C.), mechanical stirrer, thermometer, PH meter, NaOH addition funnel and phosgene bubbler. Phosgene was bubbled through the rapidly stirred mixture at a rate of about 2.0 g per minute. Sodium hydroxide (5M) was added concurrently at such a rate as to maintain the pH in the range of about 2–5. The reaction temperature increased from 8° C. at the start of reaction to 15° C. within 4 minutes. A temperature of 15°–20° C. was maintained for about 15 minutes into the reaction, until the temperature began to climb. The reaction was quenched by sparging with nitrogen for 30 minutes to remove excess phosgene. The methylene chloride solution was washed with water and 1 molar HCl. A sample was derivatized with phenol/triethylamine to form the carbonate for high pressure liquid chromatograph analysis.

Hplc analysis of the reaction product indicated 67% BPA-bischloroformate, 16% dimer bischloroformate, 5% trimer bischloroformate and 2% tetramer bischloroformate. In addition, 4% bisphenol monochloroformate was formed.

As a control, the 2-liter Morton flask was charged with an equivalent concentration of bisphenol-A as indicated above with 500 ml methylene chloride. The Morton flask was fitted with a condenser, mechanical stirrer, thermometer, pH meter, NaOH addition funnel and phosgene bubbler as indicated above. The phosgene was bubbled through the rapidly stirred mixture at a rate of about 2.0 g per minute and sodium hydroxide (5 molar) was added concurrently at a rate so as to maintain the pH in the range of 2–5. The reaction temperature increased from ambient to 40° C. within 5 minutes, and was maintained at reflux throughout the reaction. After 52 minutes, bisphenol-A was no longer present and phosgene bubbling was terminated. The reaction was quenched by sparging with nitrogen for 30 minutes and the methylene chloride solution was washed with water and 1 ml HCl. A 2 ml sample was removed for high pressure liquid chromatograph analysis. Derivatization with phenol/triethylamine to the carbonate form and analysis by Hplc indicated the following products: BPA-bischloroformate 16% (monomer), BPA-dimer-bischloroformate 20%, BPA-trimer-bischloroformate 18%, BPA-tetramer-bischloroformate 17%, BPA-pentamer-bischloroformate 14%, BPA hexamer-bischloroformate 11%, BPA heptamer-bischloroformate 9% and BPA monochloroformate 6%.

EXAMPLE 2

A 500 ml Morton flask, charged with bisphenol-A (22.82 g; 100 mmol), methylene chloride (100 ml) and fluorocarbon refrigerant 11 ($CFCl_3$; 25 ml), was fitted with a chilled spiral condenser (condenser temperature about $-6°$ C.), mechanical stirrer, thermometer, pH meter, NaOH addition funnel and phosgene bubbler. Phosgene was bubbled through the rapidly stirred mixture at a rate of about 1.0 g per minute. Sodium hydroxide (5M) was added concurrently at such a rate as to maintain the pH in the range of about 2–5. The reaction temperature increased from 8° C. at the start of reaction to 30° C. within about 4 minutes. A temperature of 30° C. was maintained for about 15 minutes into the reaction, until the temperature began to climb. The reaction was quenched by sparging with nitrogen for 30 minutes to remove excess phosgene. The methylene chloride solution was washed with water and 1 molar HCl. A sample was derivatized with phenol/triethylamine to form the carbonate for high pressure liquid chromatograph analysis.

Hplc analysis of the reaction product indicated 60.5% BPA-bischloroformate, 15.3% dimer bischloroformate, 4.5% trimer bischloroformate and 1% tetramer bischloroformate. In addition, 16.9% bisphenol monochloroformate was formed.

These examples illustrate the effectiveness of reducing the phosgenation temperature and the improved yields of monomeric and dimeric bischloroformates obtained by reducing the reaction temperature.

Variations of the above embodiment will be obvious to those skilled in the art. These obvious variations are intended to be included within the scope of this invention.

What is claimed is:

1. A method for performing phosgenation reactions at reduced reflux temperatures which comprises introducing an inert fluorocarbon refrigerant to a phosgenation reaction medium comprising a methylene chloride solvent system and a hydroxy compound of the formula $R^2(OH)_x$, wherein $R^2$ is an aliphatic, alicyclic or aromatic radical and x is at least 1; and then reacting phosgene within said reaction medium at reflux, at a temperature below about 30° C. and a pressure of about 1 atmosphere, said inert fluorocarbon refrigerant being selected from the group consisting of $CHCl_2F$, $CCl_3F$, $CClF_2$—$CClF_2$, $CCl_2$—F—$CF_3$, $CH_2Cl$—$CF_3$, $CH_3$—$ClF_2$, $CBrClF_2$, $CF_2I$—$CF_3$, $CHClF$—$CClF_2$, perfluorinated carbon compounds of from 4 to 5 carbon atoms and fluorinated ethers of from 2 to 4 carbon atoms.

2. A method as in claim 1 for producing bischloroformate wherein the perfluorinated carbon compounds are selected from the group consisting of n-perfluorobutane, perfluoroisobutane and cyclicoctafluorobutane; and the fluorinated ethers are selected from the group consisting of tetrafluorodimethyl ether, monofluorodimethyl ether, perfluorodiethyl ether, and 1,1-difluorodimethyl ether.

3. A method as in claim 1 wherein the reflux temperature falls within the range of about 10°–20° C.

4. A method as in claim 1 wherein the reactant is bisphenol-A.

5. A method as in claim 4 wherein the quantity of phosgene usage per equivalent of bisphenol-A is about 1.0 to 2.5 equivalents.

6. A method as in claim 5 wherein the phosgene flow rate falls within the range of 0.01 to 0.2 equivalents per equivalent of reactant per minute.

7. A method as in claim 1 wherein the quantity of fluorocarbon refrigerant in the methylene chloride solvent system falls within the range of 1 to 50% by weight.

8. A method for forming bischloroformates by reacting phosgene with a bisphenol of the formula HO—$A^1$—Y—$A^2$—OH, wherein each of $A^1$ and $A^2$ is a single-ring divalent aromatic radical and Y is a bridging radical in which one or two atoms separate $A^1$ from $A^2$, said method comprising passing phosgene into a refluxing solution of methylene chloride and an inert fluorocarbon refrigerant which contains said hydroxy compound at a temperature within the range of about 10°–20° C. and a pressure of about 1 atmosphere, wherein said inert fluorocarbon refrigerant is selected from the group consisting of $CCl_3F$, $CHCl_3F$, $CClF_2$—$CClF_2$, $CCl_2F$—$CF_3$, $CH_2Cl$—$CF_3$, $CF_2I$—$CF_3$, $CH_3$—$CClF_2$, $CHClF$—$CClF_2$, $CBrClF_2$, perfluorinated carbon compounds of from 4 to 5 carbon atoms and fluorinated ethers of from 2 to 4 carbon atoms.

9. A method as in claim 8 wherein the perfluorinated carbon compounds are selected from the group consisting of n-perfluorobutane, perfluoroisobutane and cyclicoctafluorobutane; and the fluorinated ethers are selected from the group consisting of tetrafluorodimethyl ether, monofluorodimethyl ether, perfluorodiethyl ether, and 1,1-difluorodimethyl ether.

10. A method as in claim 8 wherein each of $A^1$ and $A^2$ is p-phenylene and Y is 2,2-propylidene and the fluorocarbon refrigerant is $CClF_2$—$CClF_2$.

11. A method as in claim 8 wherein the quantity of the inert fluorocarbon refrigerant within the methylene chloride solvent system falls within the range of about 15 to 30% by volume.

* * * * *